(12) United States Patent
Kohlstruk et al.

(10) Patent No.: US 7,001,973 B2
(45) Date of Patent: Feb. 21, 2006

(54) CATALYST AND PROCESS FOR PREPARING LOW-VISCOSITY AND COLOR-REDUCED POLYISOCYANATES CONTAINING ISOCYANURATE GROUPS

(75) Inventors: Stephan Kohlstruk, Marl (DE); Ingo Bockhoff, Marl (DE); Michael Ewald, Marl (DE); Rainer Lomoelder, Muenster (DE)

(73) Assignee: Degussa AG, Duesseldorf (DE)

( * ) Notice: Subject to any disclaimer, the term of this patent is extended or adjusted under 35 U.S.C. 154(b) by 305 days.

(21) Appl. No.: 10/396,475

(22) Filed: Mar. 26, 2003

(65) Prior Publication Data

US 2003/0187178 A1 Oct. 2, 2003

Related U.S. Application Data

(62) Division of application No. 10/023,901, filed on Dec. 21, 2001, now Pat. No. 6,613,863.

(30) Foreign Application Priority Data

Dec. 23, 2000 (DE) ................................ 100 65 176

(51) Int. Cl.
  *C08G 18/16* (2006.01)

(52) U.S. Cl. .................. 528/52; 564/282; 564/289; 544/193; 544/222

(58) Field of Classification Search ........... 564/282, 564/289; 528/52; 544/193, 222
See application file for complete search history.

(56) References Cited

U.S. PATENT DOCUMENTS

| 3,954,684 | A | | 5/1976 | Farrissey et al. |
| 3,980,594 | A | | 9/1976 | Fabris et al. |
| 4,040,992 | A | | 8/1977 | Bechara et al. |
| 4,748,242 | A | | 5/1988 | Halpaap et al. |
| 4,960,848 | A | | 10/1990 | Scholl et al. |
| 5,240,970 | A | | 8/1993 | Nichols et al. |
| 5,288,864 | A | | 2/1994 | Nichols et al. |
| 5,298,431 | A | | 3/1994 | Goldstein et al. |
| 5,641,726 | A | * | 6/1997 | Walker ........................ 504/158 |
| 5,691,440 | A | | 11/1997 | Katz et al. |
| 5,696,292 | A | * | 12/1997 | Cody et al. ................. 564/296 |
| 6,093,817 | A | | 7/2000 | Kohlstruk et al. |
| 6,452,003 | B1 | | 9/2002 | Ewald et al. |
| 6,552,154 | B1 | | 4/2003 | Kohlstruk et al. |
| 6,613,863 | B1 | | 9/2003 | Kohlstruk et al. |

FOREIGN PATENT DOCUMENTS

| DE | 39 02 078 | 7/1990 |
| EP | 0 082 987 | 7/1983 |
| EP | 0 351 873 | 1/1990 |
| WO | WO 96/10550 | 4/1996 |

OTHER PUBLICATIONS

Patent Abstracts of Japan, JP 08-239371, Sep. 17, 1996.
Database Crossfire Bellstein Online, AN 5190380, XP-002253686, 1 page, 1992.
S. Tomas, et al., J. Org. Chem., vol. 61, No. 26, Database Crossfire Beilstein 'Online, AN 5193770, XP-002253687, 3 pages, 1996.
Database Crossfire Beilstein Online, AN 56899067, XP-002253688, 1 page, 1993.
Database Crossfire Beilstein Online, AN 5701487, XP-002253689, 1 page, 1993.
Database Crossfire Beilstein Online, AN 6089678, XP-002253690, 1 page, 1993.
A. Smirnova, et al., J. Appl. Chem., vol. 60, No. 3, Database Crossfire Beilstein Online, AN 6886506, XP-002253731, 2 pages, 1987.
Wang, et al., J. Chem., vol. 28, No. 8, Database Crossfire Beilstein Online, AN 7614045, XP-002253732, 1 page, 1996.

\* cited by examiner

*Primary Examiner*—Rachel Gorr
(74) *Attorney, Agent, or Firm*—Oblon, Spivak, McClelland, Maier & Neustadt, P.C.

(57) ABSTRACT

A low-viscosity polyisocyanate of reduced color, containing isocyanurate groups is prepared by partially trimerizing an aliphatic and/or cycloaliphatic diisocyanate in the presence of 0.02 to 2% weight, based on the weight of the diisocyanate starting material, of at least one trimerization catalyst containing a quarternary amine component and then removing excess diisocyanate from the reaction medium.

27 Claims, No Drawings

CATALYST AND PROCESS FOR PREPARING LOW-VISCOSITY AND COLOR-REDUCED POLYISOCYANATES CONTAINING ISOCYANURATE GROUPS

This application is a divisional of U.S. Ser. No. 10/023,901, filed Dec. 21, 2001, and issued as U.S. Pat. No. 6,613,863.

BACKGROUND OF THE INVENTION

1. Field of the Invention

The present invention relates to a catalyst and to a process for preparing low-viscosity and color-reduced polyisocyanates containing isocyanurate groups.

2. Description of the Background

For high-quality one- and two-component polyurethane coating materials possessing high light and weathering stability, polyisocyanate mixtures containing isocyanurate groups and uretdione groups are employed, in particular, as the isocyanate component.

For the preparation of polyisocyanates containing isocyanurate groups and uretdione groups, which are suitable as raw materials for polyurethane coating formulations, a variety of processes are known. These processes differ, generally speaking, in the selection of the trimerization catalysts or else in the selection of the organic isocyanates to be used in the oligomerization reaction (cf., e.g., GB-B 1391066, EP 82 987, DE 390 2078, DE 339 396, EP 224 165).

Isocyanates suitable for trimerization, examples being aromatic, cycloaliphatic and aliphatic polyisocyanates with an isocyanate functionality of two or more, may be prepared by various kinds of processes (Annalen der Chemie 562 (1949), pages 75 ff.). The processes which have proven to be particularly suitable in industry include preparation of an isocyanate by phosgenation of organic polyamines to the corresponding polycarbamoyl chlorides followed by thermal dehydrochlorination of the chlorides into organic polyisocyanates and hydrogen chloride.

Alternatively, organic polyisocyanates may be prepared without the use of phosgene, i.e., by phosgene-free processes. According to EP 0 126 299 (U.S. Pat. No. 4,596,678), EP 130 126 300 (U.S. Pat. No. 4,596,679) and EP 0 355 443 (U.S. Pat. No. 5,087,739), for example, (cyclo) aliphatic diisocyanates, such as 1,6-hexamethylene diisocyanate (HDI) and/or isomeric aliphatic diisocyanates having 6 carbon atoms in the alkylene radical and 1-isocyanato-3-isocyanatomethyl-3,5,5-trimethylcyclohexane (isophorone diisocyanate (IPDI)), may be prepared by reacting the parent (cyclo)aliphatic diamines with urea and alcohols to give (cyclo)aliphatic biscarbamic esters and thermally eliminating alcohol from these esters thereby yielding the corresponding diisocyanates and alcohols. The synthesis takes place continuously in a circulation process and in the presence, if desired, of N-unsubstituted carbamic esters, dialkyl carbonates, and other by-products returned from the reaction process.

Examples of catalysts which may be used for the trimerization of isocyanates to give the desired polyisocyanates containing isocyanurate and uretdione groups are tertiary amines, phosphines, alkali metal phenoxides, aminosilanes, quaternary ammonium hydroxides, and quaternary ammonium carbonates. Other highly suitable oligomerization catalysts are hydroxides, halides or carboxylates of hydroxyalkylammonium ions (cf., e.g., EP 351 873, U.S. Pat. No. 5,290,902), alkali metal salts, and also tin salts, zinc salts and/or lead salts of alkylcarboxylic acids. Depending on the catalyst, it is also possible to use various cocatalysts such as, for example, OH-functionalized compounds or Mannich bases comprising secondary amines and aldehydes and/or ketones.

For the oligomerization, the (cyclo)aliphatic diisocyanates are reacted in the presence of a catalyst, with or without the use of solvents and/or auxiliaries, until the desired conversion is attained. Partial trimerization is one of the terms used in this context, since the target conversion is generally well-below 100%. Subsequently, the reaction is terminated by deactivation of the catalyst and the excess monomeric diisocyanate is usually separated, generally by flash distillation or thin-film distillation. Deactivation is conducted by thermal treatment or by adding a catalyst inhibitor such as, for example, p-toluenesulfonic acid or bis(2-ethylhexyl)phosphate. Particularly advantageous, in the context of the trimerization of isocyanates on the industrial scale, is the use of quaternary hydroxyalkylammonium carboxylates as oligomerization catalysts. These catalysts of the choline type are thermally labile. It is unnecessary to terminate the trimerization on reaching the desired conversion by adding catalyst inhibitors which have the potential to reduce the quality. Instead, the controlled thermal deactivation permits optimum process control. This thermal stability is also advantageous from the standpoint of process safety. Uncontrolled "runaway" of the reaction is impossible, provided the amount of catalyst metered in remains below a multiple of the usual amount.

Depending on the type of catalyst used and the reaction temperature, the resulting polyisocyanates have different fractions of isocyanurate groups and uretdione groups, respectively. The products are usually clear, although products with a more or less strong yellow coloration may also be obtained depending on the type of catalyst, quality of diisocyanate, temperature of reaction, and reaction regime. For the preparation of high quality polyurethane coating materials, however, products having a very low color number are required.

In the light of ongoing legislative concerns to monitor and restrict the emission of volatile organic compounds (known as VOCs), coatings manufacturers are continually under pressure to reduce the solvent content of their formulations. Complying with the strict statutory requirements is no trivial task. Using the solvent, coating formulations are adjusted to a viscosity which ensures optimum processing properties and sprayability. If the solvent content is reduced, the viscosity rises automatically and the processing parameters of the formulation are significantly impaired. The problem can, however, be countered by using binder components of especially low viscosity to prepare the low-solvent systems, known as low VOC coating materials. On the part of the manufacturers of PU formulations, accordingly, there is an urgent need for polyisocyanates which contain isocyanurate groups and which are of good color quality and at the same time feature low viscosity. The latter is true in particular of polyisocyanates based on IPDI (isophorone diisocyanate) and NBDI (2,5(2,6)-bis(isocyanatomethyl)bicyclo[2.2.1] heptane), which have a particularly high viscosity in the form in which they have been freed from monomer.

The trimerization of diisocyanates produces not only the ideal trimer (monoisocyanurate), but also the pentamer, the heptamer, and higher oligomers. The viscosity of the demonomerized polyisocyanate increases as the oligomer content rises. In principle, the oligomer content of a polyisocyanate containing isocyanurate groups is in inverse proportion to the degree of conversion; consequently, it may be controlled via the conversion of the partial trimerization. Where a suitably low conversion is directed, the viscosity of the resultant product is also low. This procedure, however, is very uneconomic. U.S. Pat. No. 5,691,440 describes trimerization catalysts which, independently of the process and with a comparable conversion, provide a lower oligomer content and hence a lower-viscosity product than the prior art catalysts (column 2, line 67 to column 3, line 3). With the aid of these catalysts, which comprise a limited selection of specific tetraalkylammonium carboxylates (claim 1), even the demanding IPDI may be trimerized to a low-oligomer product while maintaining high and hence economic conversions (column 3, line 3-37).

The catalysts of U.S. Pat. No. 5,691,440 therefore enable economic access to low-viscosity polyisocyanates containing isocyanurate groups, even when using demanding diisocyanates such as IPDI as raw material. A disadvantage, however, is that the products have an unwanted yellow coloration. Their color quality is deserving of optimization, because, as already mentioned, products having an extremely low color number are required for the preparation of high-quality polyurethane coating materials. A need continues to exist for a catalyst system which provides a low-viscosity polyisocyanate which contains isocyanurate groups and is of improved color quality.

SUMMARY OF THE INVENTION

Accordingly, one object of the present invention is to provide a process for producing low-viscosity polyisocyanates which contain isocyanurate groups and is of improved color quality.

Briefly, this object and other objects of the present invention as hereinafter will become more readily apparent can be attained by a process for preparing low-viscosity polyisocyanates and polyisocyanates of reduced color containing isocyanurate groups, which comprises, partially trimerizing aliphatic and/or cycloaliphatic diisocyanates in the presence of 0.02 to 2% by weight, based on the weight of the diisocyanate starting material, of at least one trimerization catalyst of formula (I):

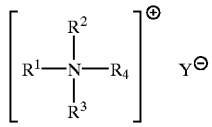

wherein $R^1 =$ 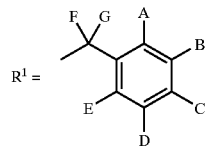

and wherein substituents A, B, C, D, and E simultaneously or independently of one another are hydrogen, chloro, $C_1$–$C_4$-alkyl, $C_1$–$C_4$-alkoxy, $C_1$–$C_4$-alkoxycarbonyl, hydroxyl, $(R^5)_3SiO$—, $(R^5)$, N—, —COOH, $(R^5)_2N$—$CH_2$— or phenyl, it being 5 possible for any two adjacent radicals selected from the group A, B, C, D and E to form a conjoint 5- or 6-membered saturated or unsaturated ring which may also include nitrogen, sulfur or oxygen heteroatoms;

F is hydrogen, methyl or fluoro;
G is hydrogen, methyl or fluoro;

$R^2$ and $R^3$ simultaneously or independently of one another are $C_1$–$C_{18}$-alkyl or $R^1$;
$R^4$ is hydrogen, methyl, $C_2$–$C_{18}$-alkyl, $C_3$–$C_8$-cycloalkyl or $C_2$–$C_{12}$-alkoxy;
$R^5$ is $C_1$–$C_{18}$-alkyl;
Y is $R^6COO$—;
$R^6$ is hydrogen or a branched or unbranched aliphatic or araliphatic $C_1$–$C_{12}$-alkyl radical, and then removing excess diisocyanate from the reaction medium.

DETAILED DESCRIPTION OF THE PREFERRED EMBODIMENTS

It has been surprisingly been found that specific quaternary benzylammonium carboxylates are capable of giving low-viscosity polyisocyanates which contain isocyanurate groups and whose color quality is markedly improved.

The preparation of the low-viscosity polyisocyanates containing isocyanurate groups by partial trimerization may take place continuously (tube reactor or tank cascade) or else may be conducted in a batchwise fashion. The catalysts of the invention are used in a low concentration ranging 0.02 to 2.0% by weight. The exact amount depends on the individual catalyst, on the conversion level desired and on the procedure employed. The catalyst may be deactivated thermally or chemically. HCl, benzoyl chloride or dibutyl phosphate is suitable, for example, for chemical inhibition. The deactivation of the catalyst, whether thermally or chemically, is necessary in order to terminate the trimerization and to ensure the storage stability of the polyisocyanate.

Under these conditions, the trimerization may be conducted within 1 to 40 minutes. The resulting compounds have one or more isocyanurate rings. Compounds having a uretdione structure may also be found as secondary components in small amounts. Compounds of this kind have been described in the literature.

Suitable starting compounds for the trimerization reaction include diisocyanates having aliphatic, cycloaliphatic or aliphatic and cycloaliphatic isocyanate groups, which have been prepared by the phosgene process or by a phosgene-free process, or else mixtures of such diisocyanates. Suitable aliphatic diisocyanates have preferably from 3 to 16, more preferably from 4 to 12, carbon atoms in their linear or branched alkylene substructure. Suitable cycloaliphatic diisocyanates have preferably from 4 to 18, more preferably from 6 to 15, carbon atoms in their cycloalkylene substructure. Suitable starting diisocyanates include aliphatic and/or cycloaliphatic diisocyanates, such as 1,4-diisocyanatocyclohexane, 1,6-diisocyanatohexane (HDI), 1,12-diisocyanatododecane, 1-isocyanato-3,3,5-trimethylcyclohexane (IPDI), 4,4'-diisocyanatodicyclohexylmethane, 1,5-diisocyanato-2,2-dimethylpentane, 1,5-diisocyanato-2-ethyl-2-propylpentane, 1,5-diisocyanato-2-butyl-2-ethylpentane, 1,6-diisocyanato-2,4,4-trimethylhexane, and 1,6-diisocyanato-2,4,4-trimethylhexane (TMDI, 1,5-diisocyanato-2-methylpentane (MPDI), and 2,5(2,6)-bis(isocyanatomethyl)bicyclo[2.2.1]heptane (NBDI). Preference is given to 1-isocyanato-3,3,5-trimethyl-5-isocyanatomethylcyclohexane (IPDI), 1,6-hexamethylene diisocyanate (HDI), 2-methylpentane 1,5-diisocyanate (MPDI), 2,5(2,6)-bis(isocyanatomethyl)bicyclo[2.2.1] heptane (NBDI), and also 2,2,4- or 2,4,4-trimethyl-1,6-hexamethylene diisocyanate (TMDI).

In order to prepare polyisocyanates containing isocyanurate groups, the catalysts of the invention are preferably used in small amounts. The exact amount may be determined easily by experimentation and is dependent on the catalytic activity of the individual catalyst, the level of conversion desired, and the procedure employed.

In accordance with the invention, the quaternary benzylammonium carboxylates of the formula are used generally in an amount of 0.02 to 2% by weight, preferably 0.04 to 1.5% by weight, based on the weight of the (cyclo)aliphatic diisocyanate used.

The trimerization of the diisocyanates is conducted in either a batchwise or continuous fashion.

In the case of a batch process, a stirred reactor is used. The mixture of diisocyanate and catalyst is charged to the reactor usually at room temperature. Subsequently, the temperature of the reaction mixture is raised to 35 to 140° C., preferably to 50 to 110° C., in order to initiate the trimerization reaction. Alternatively, the catalyst may be metered into the reaction medium after the diisocyanate has reached the necessary temperature for the reaction. The trimerization reaction is exothermic, and the catalyst is destroyed in the course of the reaction.

Continuous trimerization is judiciously conducted in a reaction coil with continuous, simultaneous metered addition of the diisocyanate and of the trimerization catalyst at 40 to 120° C. and over the course of 1 to 40 minutes. It has proven especially judicious to mix the starting components thoroughly prior to their entry into the reaction coil. For more precise metering of the small amounts of catalyst, and in order to generate a better quality of mixing, it may be advantageous to dissolve the catalyst in an appropriate organic solvent. Appropriate solvents are in principle those in which the catalyst is readily soluble. Preferably, however, the use of solvents is dispensed with to a large extent.

The continuous trimerization may also be conducted in a cascade of stirred tanks. In this case it is advantageous to conduct the trimerization isothermally at a temperature from 40 to 110° C., preferably 60 to 90° C., and to terminate the reaction when the desired conversion has been reached by adding a catalyst inhibitor. Coupling of stirred tank cascade and reaction coil is also conceivable.

To remove the unreacted diisocyanate, the reaction mixture is subjected to flash evaporation.

The monomer-freed isocyanurates prepared by the process of the invention, containing isocyanurate groups, constitute useful intermediates for polyurethane coatings, such as leather coatings and textile coatings. Polyurethane dispersions and adhesives may also be prepared. The polyurethane is also particularly valuable as the polyisocyanate component in one- and two-component polyurethane systems for weather- and light-stable polyurethane coating materials. In these applications, the process products of the invention may be used either as such or else in a form in which they have been blocked with blocking agents. Suitable examples of blocking agents in this context are lactams such as e-caprolactam, oximes such as methyl ethyl ketoxime or butanone oxime, triazoles such as 1H-1,2,4-triazole, readily enolizable compounds such as acetoacetic esters or acetylacetone, or else malonic acid derivatives such as malonic diesters having 1–10 carbon atoms in the alcohol residues.

Another aspect of the present invention is the benzylammonium carboxylate catalyst per se which is employed in the present process for the trimerization of diisocyanates. In the benzylammonium carboxylate catalyst of the invention having formula (I) above, the substituents preferably have the following definitions:

A is methyl, methoxy or hydrogen; B is hydrogen; C is methyl, methoxy or hydrogen; D is hydrogen; E is methyl, methoxy or hydrogen; F is hydrogen or methyl; G is hydrogen or methyl; $R^2$ and $R^3$ are each $R_1$ or methyl, ethyl, propyl, butyl, pentyl or hexyl; $R^4$ and $R^1$ are each methyl, ethyl, propyl, butyl, pentyl, hexyl or cyclohexyl; and $R^6$ is tert-butyl, pentyl, isopentyl, hexyl, isohexyl, ethylpentyl or isoheptyl.

The invention likewise provides a process for preparing the catalysts, in a first step of which a tertiary amine is quaternized and in a second step of which the quaternary benzylammonium compound obtained is converted into the corresponding carboxylate.

The trimerization catalysts of the invention may be used for reacting diisocyanates which have been prepared by the phosgene process or by a phosgene-free process, for example, by thermal cleavage of (cyclo)aliphatic biscarbamic esters (cf., e.g., EP-B-0 126 299 (U.S. Pat. No. 4,596,678)). Suitable starting diisocyanates are aliphatic and/or cycloaliphatic diisocyanates, e.g., 1,4-diisocyanatocyclohexane, 1,6-diisocyanatohexane (HDI), 1,12-diisocyanatododecane, 1-isocyanato-3,3,5-trimethylcyclohexane (IPDI), 4,4'-diisocyanatodicyclohexylmethane, 1,5-diisocyanato-2,2-dimethylpentane, 1,5-diisocyanato-2-ethyl-2-propylpentane, 1,5-diisocyanato-2-butyl-2-ethylpentane, 1,6-diisocyanato-2,4,4-trimethylhexane, and 1,6-diisocyanato-2,4,4-trimethylhexane (TMDI), 1,5-diisocyanato-2-methylpentane (MPDI), and 2,5(2,6)-bis (isocyanatomethyl)bicyclo[2.2.1]heptane (NBDI).

A two-stage synthesis path may be followed for preparing trimerization catalysts of the invention. In the first step, a tertiary amine is quaternized. Suitable alkylating agents include alkyl halides, benzyl halides, alkyl triflates, benzyl triflates, and also alkyl and benzyl tosylates. Suitable examples include methyl iodide, methyl bromide, methyl chloride, methyl triflate, methyl tosylate, ethyl iodide, ethyl bromide, ethyl chloride, ethyl triflate, ethyl tosylate, butyl iodide, butyl bromide, butyl chloride, butyl triflate, butyl tosylate, dodecyl iodide, dodecyl bromide, dodecyl chloride, dodecyl triflate, dodecyl tosylate, allyl iodide, allyl bromide, allyl chloride, allyl triflate, allyl tosylate, benzyl iodide, benzyl bromide, benzyl chloride, benzyl triflate, benzyl tosylate, 4-chlorobenzyl iodide, 4-chlorobenzyl bromide, 4-chlorobenzyl chloride; 4-chlorobenzyl triflate, 4-chlorobenzyl tosylate, 2-chlorobenzyl iodide, 2-chlorobenzyl bromide, 2-chlorobenzyl chloride, 2-chlorobenzyl triflate, 2-chlorobenzyl tosylate, methallyl iodide, methallyl bromide, methallyl chloride, methallyl triflate, methallyl tosylate, 4-methoxycarbonylbenzyl iodide, 4-methoxycarbonylbenzyl bromide, 4-methoxycarbonylbenzyl chloride, 4-methoxycarbonylbenzyl triflate, 4-methoxycarbonylbenzyl tosylate, 4-methoxybenzyl iodide, 4-methoxybenzyl bromide, 4-methoxybenzyl chloride, 4-methoxybenzyl triflate, 4-methoxybenzyl tosylate, 4-methylbenzyl iodide, 4-methylbenzyl bromide, 4-methylbenzyl chloride, 4-methylbenzyl triflate, 4-ethylbenzyl tosylate, 3-methylbenzyl iodide, 3-methylbenzyl bromide, 3-methylbenzyl chloride, 3-methylbenzyl triflate, 3-methylbenzyl tosylate, 2-methylbenzyl iodide, 2-methylbenzyl bromide, 2-methylbenzyl chloride, 2-methylbenzyl triflate, and 2-methylbenzyl tosylate. Suitable alkylating agents also include Meerwein salts such as trimethyloxonium tetrafluoroborate and triethyloxonium tetrafluoroborate. Examples of tertiary amines suitable in principle are trimethylamine, triethylamine, dimethylethylamine, diethylmethylamine, tripropylamine, tributylamine, trioctylamine, tridodecylamine, N,N-dimethylallylamine, N,N-diethylallylamine, N-ethyl-N-methylallylamine, N,N-dimethylmethallylamine, N,N-diethylmethallylamine, N-ethyl-N-methylmethallylamine, tridodecylamine, dimethyldodecylamine, diethyldodecylamine, dipropyldodecylamine, dibutyldodecylamine, didodecylmethylamine, didodecylethylamine, didodecylpropylamine, didodecylbutylamine, N,N-dimethyl-2-methoxybenzylamine, N,N-dimethyl-3-methoxybenzylamine, N,N-dimethyl-4-methoxybenzylamine, N,N-dimethyl-2,3-dimethoxybenzylamine, N,N-dimethyl-3,4-dimethoxybenzylamine, N,N-dimethyl-3,5-dimethoxybenzylamine, N,N-dimethylbenzylamine, N,N-dimethylbenzylamine-4-carbonitrile, 4-methoxycarbonyl-N,N-dimethylbenzylamine, 4-ethoxycarbonyl-N,N-dimethylbenzylamine, 3-(N,N-imethylaminomethyl)-N,N-dimethylbenzylamine, 1-phenylethyldimethylamine, 4-hydroxy-N,N-dimethylbenzylamine, 4-trimethylsiloxy-N,N-dimethylbenzylamine, and N,N-dimethylnaphthylamine. The quaternization of the tertiary amines takes place at from 0 to 100° C. and may be carried out in the presence or absence of solvents. The solvent-based process is generally preferred. Examples of suitable solvents include acetonitrile, dimethylformamide, dimethyl sulfoxide, acetone, 2-ethylhexanediol, and dichloromethane.

The resulting quaternary benzylammonium halides, tosylates, triflates or tetrafluoroborates are converted into the desired quaternary benzylammonium carboxylates in the second step. This is done preferably by means of ion exchange chromatography. For this purpose a basic ion exchange resin (e.g., Amberlyst, Dowex or Sephadex type) is activated with potassium hydroxide or sodium hydroxide solution and loaded with the desired carboxylic acid. Examples of suitable carboxylic acids include pivalic acid, hexanoic acid, acetic acid, 2-ethylhexanoic acid, propanoic acid, adipic acid, succinic acid, and oleic acid. The chromatography column is subsequently loaded with the quaternary benzylammonium salt and eluted. The eluate contains the quaternary benzylammonium carboxylate of the invention. The solvent may be removed from the reaction product by application of a vacuum. In the case of the quaternary benzylammonium halides, the catalysts of the invention may also be prepared by cationic exchange in solution in a highly pure form if the co-reactants used comprise the silver carboxylates of the abovementioned carboxylic acids. It is also possible first to convert the quaternary benzylammonium halides, tosylates, triflates or tetraborates into the corresponding quaternary benzylammonium hydroxides by means of ion exchange chromatography and then to subsequently convert these hydroxides into the quaternary benzylammonium carboxylates of the invention by reaction with the desired carboxylic acid and removal, where appropriate, of the water that is released.

Having now generally described this invention, a further understanding can be obtained by reference to certain specific examples which are provided herein for purposes of illustration only and are not intended to be limiting unless otherwise specified A. Preparation of the Catalysts All reactions were conducted under an inert gas atmosphere, preferably under nitrogen.

A.1. Preparation of Benzyldimethylammonium Pivalate (cat. 1)

In a three-necked flask equipped with a Claisen attachment, reflux condenser, internal thermometer, mechanical stirrer attachment, dropping funnel, gas inlet, and gas outlet, benzyldimethylamine (0.2 mol) was admixed dropwise with stirring at room temperature with triethyloxonium tetrafluoroborate (200 ml of a 1 M solution in methylene chloride) at a rate such that the temperature of the reaction mixture did not exceed 45° C. After 7 d, the methylene chloride was removed in vacuo and the viscous, pale yellow residue was dissolved in methanol.

A chromatography column (diameter about 3.5 cm) was packed with Dowex 1X8-50 and loaded in succession with an aqueous 2M NaOH solution, a 3% strength solution of pivalic acid in ethanol, methanol, and the methanolic solution of the quaternary ammonium tetrafluoroborate. The catalyst of the invention was eluted with MeOH, and the eluate was concentrated in vacuo. The residue was dissolved in diethyl ether, the insoluble fraction (about 2.8 g) was removed by filtration, and the ether was removed in vacuo. Yield: 38.2 g (72%) of cat. 1 as a pale yellow, viscous liquid.

A.2 Preparation of benzyldimethylethylammonium 2-ethylhexanoate (cat. 2)

The preparation was conducted as described for cat.1 (A.1.). Instead of pivalic acid, 2-ethylhexanoic acid was used. Yield: 33.5 g (55%) of cat.2 as a pale yellow, viscous liquid.

A.3. Preparation of benzyltributylammonium 2-ethylhexanoate (cat.3)

In a three-necked flask equipped with a Claisen attachment, internal thermometer, dropping funnel and mechanical stirrer, and also a gas inlet and gas outlet, a solution of tributylamine (0.2 mol) in 70 ml of dimethylformamide was admixed dropwise with stirring with benzyl chloride at a rate such that the temperature of the reaction mixture did not exceed 50° C. When addition was complete, the reaction temperature was raised to 60 to 70° C. After 6 h, the solvent was removed in vacuo and the residue was dissolved in water. Silver 2-ethylhexanoate (0.2 mol; from 2-ethylhexanoic acid and silver carbonate) was added dropwise with stirring to the aqueous solution of the quaternary ammonium chloride. The mixture was permitted to stand overnight and the precipitate was separated by filtration. The filtrate was concentrated to dryness in vacuo. Yield: 82.1 g (98%) of cat. 3 as a pale yellow, viscous oil.

A.4. Preparation of N,N-dimethyl-N-ethyl-N-(4-methoxybenzyl)ammonium 2-ethylhexanoate (cat. 4)

The preparation was conducted as described for cat.1(A.1.). Instead of pivalic acid, 2-ethylhexanoic acid was used, and instead of benzyldimethylamine, N,N-dimethyl-N-(4-methoxybenzyl)amine was used. Yield: 45.3 g (67%) of cat. 4 as a pale yellow, viscous oil.

A.5. Preparation of N,N,N-tributyl-N-(4-methoxybenzyl) ammonium pivalate (cat. 5)

The preparation was conducted as described for cat.3 (A.3.). Instead of 2-ethylhexanoic acid, pivalic acid was used, and instead of benzyl chloride, 4-methoxybenzyl chloride was used. Yield: 79.0 g (97%) of cat.5 as a pale yellow, viscous oil.

B. Trimerization examples: Inventive Examples 1–10 and Comparative Examples A–E

B.1. Trimerization of the Isocyanates

Catalyst and (cyclo)aliphatic diisocyanate are introduced into the reactor at room temperature. The temperature of the mechanically stirred reaction mixtures, which is maintained under an inert gas atmosphere ($N_2$), is raised continuously over the course of 10 to 15 minutes to the starting temperature (about 70° C.). Following initiation of the exothermic trimerization reaction, the source of heat is removed. The temperature of the reaction mixture passes through a maximum and falls off again following the thermal deactivation of the catalyst, which takes place in the course of the reaction. The reaction mixture is cooled to room temperature and the excess monomer is separated from the polyisocyanate by flash evaporation.

Comparative catalysts used were those described in U.S. Pat. No. 5,691,440: N(2-hydroxypropyl)-N,N,N-trimethylammonium 2-ethylhexanoate (C-cat. 1), Aliquat 336 pivalate (C-cat. 2), and tetrabutylammonium pivalate (C-cat. 3). The catalysts were synthesized as specified in U.S. Pat. No. 5,691,440.

The results of the trimerization experiments are summarized in Table 1 and attest to the performance of the catalysts of the invention with respect to viscosity and color of the polyisocyanates formed. Alcohols such as benzyl alcohol and methanol may be used as cocatalysts or to dilute the catalysts of the invention.

TABLE 1

| Input | Catalyst | Conversion [%] | Viscosity at 23° C.[1] [mPas] | Color number[2] [Hazen} |
|---|---|---|---|---|
| Comparative Example | | | | |
| A | C-cat. 1 | 35 | 914 | 110 |
| B | C-cat. 1 | 44 | 983 | 102 |
| C | C-cat. 2 | 34 | 523 | 83 |
| D | C-cat. 2 | 43 | 732 | 98 |
| E | C-cat. 3 | 40 | 556 | 83 |
| Inventive Example | | | | |
| 1 | Cat. 1 | 33 | 503 | 51 |
| 2 | Cat. 1 | 48 | 697 | 39 |
| 3 | Cat. 2 | 35 | 529 | 56 |
| 4 | Cat. 2 | 50 | 709 | 47 |
| 5 | Cat. 3 | 25 | 604 | 77 |
| 6 | Cat. 3 | 34 | 740 | 73 |
| 7 | Cat. 4 | 36 | 525 | 60 |
| 8 | Cat. 4 | 43 | 632 | 47 |
| 9 | Cat. 5 | 35 | 532 | 46 |
| 10 | Cat. 5 | 40 | 609 | 38 |

[1]Monomer-free polyisocyanate based on isophorone diisocyanate, 70% in butyl acetate;
[2]Monomer-free polyisocyanate based on isophorone diisocyanate, 50% in butyl acetate The disclosure of German priority Application Number 100 65 176.3 filed Dec. 23, 2000 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by letters patent is:

1. A trimerization catalyst, comprising a compound selected from the group consisting of benzyldimethylethylammonium pivalate, benzyldimethylethylammonium 2-ethylhexanoate, benzyltributylammonium 2-ethylhexanoate, N,N-dimethyl-N-ethyl-N-(4-methoxybenzyl)ammonium-2-ethylhexanoate, or N,N,N-tributyl-N-(4-methoxybenzyl)ammonium pivalate.

2. A process for preparing a trimerization catalyst comprising:
quaternizing a tertiary amine with an alkylating agent thereby forming a quaternary benzylammonium compound; and
converting the quaternary benzylammonium compound into the corresponding carboxylate salt;
wherein said alkylating agent is selected from the group consisting of Meerwein salts;
thereby obtaining said trimerization catalyst which is a compound of formula (I):

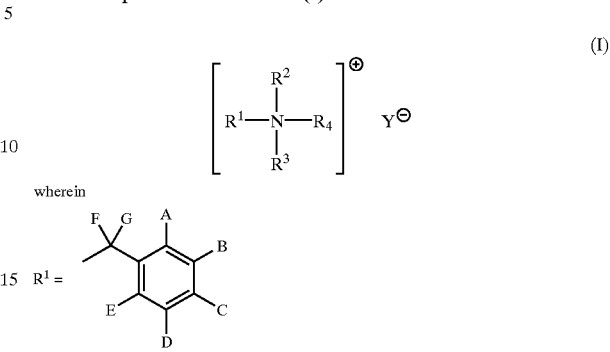

wherein $R^1 =$ and wherein substituents A, B, C, D, and E simultaneously or independently of one another are hydrogen, chloro, $C_1$–$C_4$-alkyl, $C_1$–$C_4$-alkoxy, $C_1$–$C_4$-alkoxycarbonyl, hydroxyl, $(R^5)_3SiO$—, $(R^5)_2N$—, COOH, $(R^5)_2N$—$CH_2$- or phenyl, it being 5 possible for any two adjacent radicals selected from the group A, B, C, D and E to form a conjoint 5- or 6-membered saturated or unsaturated ring which may also include nitrogen, sulfur or oxygen heteroatoms;

F is hydrogen, methyl or fluoro;

G is hydrogen, methyl or fluoro;

$R^2$ and $R^3$ simultaneously or independently of one another are $C_1$–$C_{18}$-alkyl or $R^1$;

$R^4$ is hydrogen, methyl, $C_2$–$C_{18}$-alkyl, $C_3$–$C_8$-cycloalkyl or $C_2$–$C_{12}$-alkoxy;

$R^5$ is $C_1$–$C_{18}$-alkyl;

Y— is $R^6COO$—;

$R^6$ is hydrogen or a branched or unbranched aliphatic or araliphatic $C_1$–$C_{12}$-alkyl radical.

3. The process according to claim 2, wherein said tertiary amine is selected from the group consisting of trimethylamine, triethylamine, dimethylethylamine, diethylmethylamine, tripropylamine, tributylamine, trioctylamine, tridodecylamine, N,N-dimethylallylamine, N,N-diethylallylamine, N-ethyl-N-methylallylamine, N,N-dimethylmethallylamine, N,N-diethylmethallylamine, dimethyldodecylamine, diethyldodecylamine, dipropyldodecylamine, dibutyldodecylamine, didodecylmethylamine, didodecylethylamine, didodecylpropylamine, didodecylbutylamine, N,N-dimethyl-2-methoxybenzylamine, N,N-dimethyl-3-methoxybenzylamine, N,N-dimethyl-4-methoxybenzylamine, N,N-dimethyl-2,3-dimethoxybenzylamine, N,N-dimethyl-3,4-dimethoxybenzylamine, N,N-dimethyl-3,5-dimethoxybenzylamine, N,N-dimethylbenzylamine, N,N-dimethylbenzylamine-4-carbonitrile, 4-methoxycarbonyl-N,N-dimethylbenzylamine, 4-ethoxycarbonyl-N,N-dimethylbenzylamine, 3-(N,N-dimethylaminomethyl)-N,N-dimethylbenzylamine, 1-phenylethyldimethylamine, 4-hydroxy-N,N-dimethylbenzylamine, 4-trimethylsiloxy-N, N-dimethylbenzylamine, and N,N-dimethylnaphthylamine.

4. The process according to claim 2, wherein said alkylating agent is selected from the group consisting of alkyl halides, benzyl halides, alkyl triflates, benzyl triflates, alkyl tosylates and benzyl tosylates.

5. The process according to claim 2, wherein said alkylating agent is selected from the group consisting of methyl iodide, methyl bromide, methyl chloride, methyl triflate, methyl tosylate, ethyl iodide, ethyl bromide, ethyl chloride, ethyl triflate, ethyl tosylate, butyl iodide, butyl bromide, butyl chloride, butyl triflate, butyl tosylate, dodecyl iodide, dodecyl bromide, dodecyl chloride, dodecyl triflate, dodecyl tosylate, allyl iodide, allyl bromide, allyl chloride, allyl triflate, allyl tosylate, benzyl iodide, benzyl bromide, benzyl chloride, benzyl triflate, benzyl tosylate, 4-chlorobenzyl iodide, 4-chlorobenzyl bromide, 4-chlorobenzyl chloride; 4-chlorobenzyl triflate, 4-chlorobenzyl tosylate, 2-chlorobenzyl iodide, 2-chlorobenzyl bromide, 2-chlorobenzyl chloride, 2-chlorobenzyl triflate, 2-chlorobenzyl tosylate, methallyl iodide, methallyl bromide, methallyl chloride, methallyl triflate, methallyl tosylate, 4-methoxycarbonylbenzyl iodide, 4-methoxycarbonylbenzyl bromide, 4-methoxycarbonylbenzyl chloride, 4-methoxycarbonylbenzyl triflate, 4-methoxycarbonylbenzyl tosylate, 4-methoxybenzyl iodide, 4-methoxybenzyl bromide, 4-methoxybenzyl chloride, 4-methoxybenzyl triflate, 4-methoxybenzyl tosylate, 4-methylbenzyl iodide, 4-methylbenzyl bromide, 4-methylbenzyl chloride, 4-methylbenzyl triflate, 4-ethylbenzyl tosylate, 3-methylbenzyl iodide, 3-methylbenzyl bromide, 3-methylbenzyl chloride, 3-methylbenzyl triflate, 3-methylbenzyl tosylate, 2-methylbenzyl iodide, 2-methylbenzyl bromide, 2-methylbenzyl chloride, 2-methylbenzyl triflate, and 2-methylbenzyl tosylate.

6. The process according to claim 2, wherein said Meerwein salts are trimethyloxonium tetrafluoroborate or triethyloxonium tetrafluoroborate.

7. The process according to claim 2, wherein said quaternizing of the tertiary amine takes place at from 0 to 100° C.

8. The process according to claim 2, wherein said quaternizing is carried out in the presence of a solvent.

9. The process according to claim 2, wherein said quaternizing is carried out in the absence of a solvent.

10. The process according to claim 8, wherein said solvent is selected from the group consisting of acetonitrile, dimethylformamide, dimethyl sulfoxide, acetone, 2-ethylhexanediol, and dichloromethane.

11. The process according to claim 2, wherein said converting of said quaternary benzylammonium compound is performed by ion exchange chromatography.

12. The process according to claim 2, wherein said carboxylate salt is obtained from a carboxylic acid selected from the group consisting of pivalic acid, hexanoic acid, acetic acid, 2-ethylhexanoic acid, propanoic acid, adipic acid, succinic acid, and oleic acid.

13. A method for trimerizing diisocyanates, comprising:
trimerizing diisocyanates in the presence of a trimerization catalyst which is a compound of formula (I):

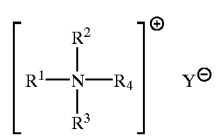

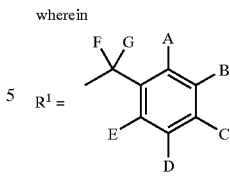

and wherein substituents A, B, C, D, and E simultaneously or independently of one another are hydrogen, chloro, $C_1$–$C_4$-alkyl, $C_1$–$C_4$-alkoxy, $C_1$–$C_4$-alkoxycarbonyl, hydroxyl, $(R^5)_3SiO$—, $(R^5)_2N$—, COOH, $(R^5)_2N$—$CH_2$- or phenyl, it being 5 possible for any two adjacent radicals selected from the group A, B, C, D and E to form a conjoint 5- or 6-membered saturated or unsaturated ring which may also include nitrogen, sulfur or oxygen heteroatoms;
F is hydrogen, methyl or fluoro;
G is hydrogen, methyl or fluoro;
$R^2$ and $R^3$ simultaneously or independently of one another are $C_1$–$C_{18}$-alkyl or $R^1$;
$R^4$ is hydrogen, methyl, $C_2$–$C_{18}$-alkyl, $C_3$–$C_8$-cycloalkyl or $C_2$–$C_2$-alkoxy;
$R^5$ is $C_1$–$C_{18}$-alkyl;
Y- is $R^6COO$—;
$R^6$ is hydrogen or a branched or unbranched aliphatic or araliphatic $C_1$–$C_2$-alkyl radical.

14. A process for preparing a trimerization catalyst, comprising:
quaternizing a tertiary amine with an alkylating agent thereby forming a quaternary benzylammonium compound; and
converting the quaternary benzylammonium compound into the corresponding carboxylate salt;
wherein said converting of said quaternary benzylammonium compound is performed by ion exchange chromatography;
thereby obtaining said trimerization catalyst which is a compound of formula (I):

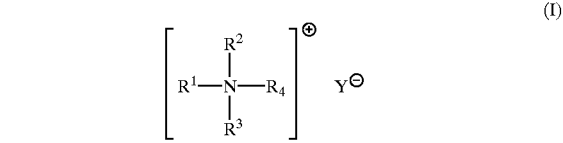

wherein

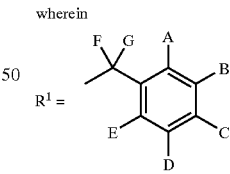

and wherein substituents A, B, C, D, and E simultaneously or independently of one another are hydrogen, chloro, $C_1$–$C_4$-alkyl, $C_1$–$C_4$-alkoxy, $C_1$–$C_4$-alkoxycarbonyl, hydroxyl, $(R^5)_3SiO$—, $(R^5)_2N$—, COOH, $(R^5)_2N$—$CH_2$- or phenyl, it being 5 possible for any two adjacent radicals selected from the group A, B, C, D and E to form a conjoint 5- or 6-membered saturated or unsaturated ring which may also include nitrogen, sulfur or oxygen heteroatoms;
F is hydrogen, methyl or fluoro;
G is hydrogen, methyl or fluoro;
$R^2$ and $R^3$ simultaneously or independently of one another are $C_1$–$C_{18}$-alkyl or $R^1$;

R⁴ is hydrogen, methyl, $C_2$–$C_{18}$-alkyl, $C_3$–$C_8$-cycloalkyl or $C_2$–$C_{12}$-alkoxy;

R⁵ is $C_1$–$C_{18}$-alkyl;

Y- is R⁶COO—;

R⁶ is hydrogen or a branched or unbranched aliphatic or araliphatic $C_1$–$C_{12}$-alkyl radical.

15. The process according to claim 14, wherein said tertiary amine is selected from the group consisting of trimethylamine, triethylamine, dimethylethylamine, diethylmethylamine, tripropylamine, tributylamine, trioctylamine, tridodecylamine, N,N-dimethylallylamine, N,N-diethylallylamine, N-ethyl-N-methylallylamine, N,N-dimethylmethallylamine, N,N-diethylmethallylamine, dimethyldodecylamine, diethyldodecylamine, dipropyldodecylamine, dibutyldodecylamine, didodecylmethylamine, didodecylethylamine, didodecylpropylamine, didodecylbutylamine, N,N-dimethyl-2-methoxybenzylamine, N,N-dimethyl-3-methoxybenzylamine, N,N-dimethyl-4-methoxybenzylamine, N,N-dimethyl-2,3-dimethoxybenzylamine, N,N-dimethyl-3,4-dimethoxybenzylamine, N,N-dimethyl-3,5-dimethoxybenzylamine, N,N-dimethylbenzylamine, N,N-dimethylbenzylamine-4-carbonitrile, 4-methoxycarbonyl-N,N-dimethylbenzylamine, 4-ethoxycarbonyl-N,N-dimethylbenzylamine, 3-(N,N-dimethylaminomethyl)-N,N-dimethylbenzylamine, 1-phenylethyldimethylamine, 4-hydroxy-N,N-dimethylbenzylamine, 4-trimethylsiloxy-N,N-dimethylbenzylamine, and N,N-dimethylnaphthylamine.

16. The process according to claim 14, wherein said alkylating agent is selected from the group consisting of alkyl halides, benzyl halides, alkyl triflates, benzyl triflates, alkyl tosylates and benzyl tosylates.

17. The process according to claim 14, wherein said alkylating agent is selected from the group consisting of methyl iodide, methyl bromide, methyl chloride, methyl triflate, methyl tosylate, ethyl iodide, ethyl bromide, ethyl chloride, ethyl triflate, ethyl tosylate, butyl iodide, butyl bromide, butyl chloride, butyl triflate, butyl tosylate, dodecyl iodide, dodecyl bromide, dodecyl chloride, dodecyl triflate, dodecyl tosylate, allyl iodide, allyl bromide, allyl chloride, ally triflate, ally tosylate, benzyl iodide, benzyl bromide, benzyl chloride, benzyl triflate, benzyl tosylate, 4-chlorobenzyl iodide, 4-chlorobenzyl bromide, 4-chlorobenzyl chloride; 4-chlorobenzyl triflate, 4-chlorobenzyl tosylate, 2-chlorobenzyl iodide, 2-chlorobenzyl bromide, 2-chlorobenzyl chloride, 2-chlorobenzyl triflate, 2-chlorobenzyl tosylate, methallyl iodide, methallyl bromide, methallyl chloride, methallyl triflate, methallyl tosylate, 4-methoxycarbonylbenzyl iodide, 4-methoxycarbonylbenzyl bromide, 4-methoxycarbonylbenzyl chloride, 4-methoxycarbonylbenzyl triflate, 4-methoxycarbonylbenzyl tosylate, 4-methoxybenzyl iodide, 4-methoxybenzyl bromide, 4-methoxybenzyl chloride, 4-methoxybenzyl triflate, 4-methoxybenzyl tosylate, 4-methylbenzyl iodide, 4-methylbenzyl bromide, 4-methylbenzyl chloride, 4-methylbenzyl triflate, 4-ethylbenzyl tosylate, 3-methylbenzyl iodide, 3-methylbenzyl bromide, 3-methylbenzyl chloride, 3-methylbenzyl triflate, 3-methylbenzyl tosylate, 2-methylbenzyl iodide, 2-methylbenzyl bromide, 2-methylbenzyl chloride, 2-methylbenzyl triflate, and 2-methylbenzyl tosylate.

18. The process according to claim 14, wherein said alkylating agent is selected from the group consisting of Meerwein salts.

19. The process according to claim 18, wherein said Meerwein salts are trimethyloxonium tetrafluoroborate or triethyloxonium tetrafluoroborate.

20. The process according to claim 14, wherein said quaternizing of the tertiary amine takes place at from 0 to 100° C.

21. The process according to claim 14, wherein said quaternizing is carried out in the presence of a solvent.

22. The process according to claim 14, wherein said quaternizing is carried out in the absence of a solvent.

23. The process according to claim 21, wherein said solvent is selected from the group consisting of acetonitrile, dimethylformamide, dimethyl sulfoxide, acetone, 2-ethylhexanediol, and dichloromethane.

24. The process according to claim 14, wherein said carboxylate salt is obtained from a carboxylic acid selected from the group consisting of pivalic acid, hexanoic acid, acetic acid, 2-ethylhexanoic acid, propanoic acid, adipic acid, succinic acid, and oleic acid.

25. The process as claimed in claim 2, wherein the substituents of formula (I) have the following definitions:

A: methyl, methoxy, H;

B: H;

C: methyl, methoxy, H;

D: H;

E: methyl, methoxy, H;

F: H, methyl;

G: H, methyl;

R², R³: R¹ or methyl, ethyl, propyl, butyl, pentyl, hexyl;

R⁴, R⁵: methyl, ethyl, propyl, butyl, pentyl, hexyl, cyclohexyl;

R⁶: tert-butyl, pentyl, isopentyl, hexyl, isohexyl, ethylpentyl, isoheptyl.

26. The process as claimed in claim 13, wherein the substituents of formula (I) have the following definitions:

A: methyl, methoxy, H;

B: H;

C: methyl, methoxy, H;

D: H;

E: methyl, methoxy, H;

F: H, methyl;

G: H, methyl;

R², R³: R¹ or methyl, ethyl, propyl, butyl, pentyl, hexyl;

R⁴, R⁵: methyl, ethyl, propyl, butyl, pentyl, hexyl, cyclohexyl;

R⁶: tert-butyl, pentyl, isopentyl, hexyl, isohexyl, ethylpentyl, isoheptyl.

27. The process as claimed in claim 14, wherein the substituents of formula (I) have the following definitions:

A: methyl, methoxy, H;

B: H;

C: methyl, methoxy, H;

D: H;

E: methyl, methoxy, H:

F: H, methyl;

G: H, methyl

R², R³: R¹ or methyl, ethyl, propyl, butyl, pentyl, hexyl;

R⁴, R⁵: methyl, ethyl, propyl, butyl, pentyl, hexyl, cyclohexyl;

R⁶: tert-butyl, pentyl, isopentyl, hexyl, isohexyl, ethylpentyl, isoheptyl.

* * * * *

UNITED STATES PATENT AND TRADEMARK OFFICE
CERTIFICATE OF CORRECTION

PATENT NO. : 7,001,973 B2
DATED : February 21, 2006
INVENTOR(S) : Kohlstruk et al.

It is certified that error appears in the above-identified patent and that said Letters Patent is hereby corrected as shown below:

<u>Title page,</u>
Items [45] and [*] Notice, should read:
-- [45] **Date of Patent: *Feb. 21, 2006**

[*] Notice:   Subject to any disclaimer, the term of this patent is extended or adjusted under 35 U.S.C. 154(b) by 305 days.

This patent is subject to a terminal disclaimer. --.

Signed and Sealed this

Twenty-fifth Day of April, 2006

JON W. DUDAS
*Director of the United States Patent and Trademark Office*